(12) United States Patent
Laugharn, Jr. et al.

(10) Patent No.: US 9,486,756 B2
(45) Date of Patent: Nov. 8, 2016

(54) METHOD AND APPARATUS FOR SHEARING OF GENOMIC MATERIAL USING ACOUSTIC PROCESSING

(71) Applicant: Covaris, Inc., Woburn, MA (US)

(72) Inventors: James A. Laugharn, Jr., Winchester, MA (US); Guillaume Durin, Lyons (FR)

(73) Assignee: Covaris, Inc., Woburn, MA (US)

( * ) Notice: Subject to any disclaimer, the term of this patent is extended or adjusted under 35 U.S.C. 154(b) by 191 days.

(21) Appl. No.: 14/534,506

(22) Filed: Nov. 6, 2014

(65) Prior Publication Data

US 2015/0132762 A1 May 14, 2015

Related U.S. Application Data

(60) Provisional application No. 61/901,691, filed on Nov. 8, 2013.

(51) Int. Cl.
| | | |
|---|---|---|
| C12Q 1/68 | (2006.01) |
| B01F 11/02 | (2006.01) |
| G01N 1/28 | (2006.01) |
| B02C 17/14 | (2006.01) |
| B02C 19/18 | (2006.01) |
| G01N 1/40 | (2006.01) |

(52) U.S. Cl.
CPC ............ *B01F 11/0283* (2013.01); *B02C 17/14* (2013.01); *B02C 19/18* (2013.01); *G01N 1/286* (2013.01); *G01N 2001/2866* (2013.01); *G01N 2001/4094* (2013.01)

(58) Field of Classification Search
CPC ... B01F 11/0283; B02C 17/14; B02C 19/18; G01N 1/286; G01N 2001/2866; G01N 2001/4094
See application file for complete search history.

(56) References Cited

U.S. PATENT DOCUMENTS

| | | | |
|---|---|---|---|
| 5,705,628 A | 1/1998 | Hawkins | |
| 2009/0093036 A1* | 4/2009 | Stone | ................... G01N 1/405 435/173.7 |
| 2009/0317884 A1 | 12/2009 | Laugharn | |
| 2013/0203045 A1* | 8/2013 | Landers | ............... C12Q 1/6816 435/5 |

\* cited by examiner

*Primary Examiner* — Cynthia B Wilder
(74) *Attorney, Agent, or Firm* — Wolf, Greenfield & Sacks, P.C.

(57) ABSTRACT

Method and apparatus for controlling acoustic treatment of a sample including a liquid. A processing volume in which the sample is acoustically treated may be controlled, e.g., by using a bead positioned in the sample that helps to enhance the shearing effects of acoustic energy on genomic fragments.

39 Claims, 6 Drawing Sheets

METHOD AND APPARATUS FOR SHEARING OF GENOMIC MATERIAL USING ACOUSTIC PROCESSING

BACKGROUND

1. Field of the Invention

Systems and methods for processing of samples with acoustic energy are generally disclosed.

2. Related Art

Acoustic energy-based sample processing devices, such as Adaptive Focused Acoustic apparatuses made by Covaris of Woburn, Mass., are effective for homogenization and disruption of biological tissues, cells and other sample material. With such devices, a controlled acoustic field enables repeatable processes to be developed which often result in higher recovery of target molecules. Such target molecules may be, for example, DNA, RNA, proteins, and the like. Target molecules or other materials may be contained as samples within a vessel.

SUMMARY OF INVENTION

Generally speaking, shearing of DNA and other genomic fragments using acoustic treatment is known from U.S. Patent Publication 2009/0317884. For example, U.S. Patent Publication 2009/0317884 discloses placing DNA fragments having a base pair length of 10 kbp and up into a 50-100 microliter vessel along with an energy director in the form of a polymer rod or bead, and acoustically treating the DNA fragments so as to shear the DNA fragments into smaller fragment sizes of about 3 kbp. See paragraphs 0009, 0038 and 0061 of U.S. Patent Publication 2009/0317884. What U.S. Patent Publication 2009/0317884 does not describe is that there was an understanding in the art at the time of filing of U.S. Patent Publication 2009/0317884 that there was a non-linear relationship between the sonic energy applied to a sample and the resulting base pair length of the sheared DNA after processing. (The energy applied to a sample via acoustic energy is measured in Joules and given by the product of peak incident power (PIP in watts) by the duty cycle of the applied energy (DC in percentage terms) by the total processing time (T in seconds) or $E=PIP*DC*T$.) This non-linear relationship, which was determined based on experimentation, was understood to require that a much higher energy level was required to shear DNA into smaller fragments, i.e., shearing a set of DNA fragments into sizes of 500 bp or less would require significantly more energy than shearing the same set of DNA fragments into sizes of about 3 kbp. In fact, the understanding was that it would generally require about 20 times or more energy to fragment a set of DNA to base pair lengths of about 300 bp as compared to fragmenting the set of DNA to base pair length of about 1500 bp. It was for this reason that U.S. Patent Publication 2009/0317884 did not describe shearing to base pair lengths below about 1.5 kbp to 3 kbp. For example, paragraph 0038 of U.S. Patent Publication 2009/0317884 provides an example in which a sample is treated using energy having a PIP of about 18 W (an intensity level of 0.5 corresponds to a PIP of about 18 W), a duty cycle of 10% and a processing time of about 4-8 minutes. This gives an energy of about 432 Joules to 864 Joules to shear the DNA to a size of about 3 kbp. The example at paragraph 0061 of U.S. Patent Publication 2009/0317884 used an energy of about 147 Joules (PIP of 3.5 W, 10% DC and T of 420 seconds) to shear DNA to 3 kbp fragments. However, because shearing to smaller fragments than 1 kbp was found to require much more energy, i.e., about 20 times or more energy to shear the same DNA to base pair lengths under 500 bp, such shearing was not done. Such large energies were not feasible because they would have increased processing times to more than 1-2 hours. (Increasing energy delivered to the sample by increasing PIP and/or duty cycle levels was not possible because such power levels caused the sample to overheat and/or splash out of the vessel.)

The inventors have surprisingly found, however, that DNA and other genomic fragments can be sheared to relatively small sizes, such as 500 bp or less, using energy levels and processing times that are comparable to or smaller than even what U.S. Patent Publication 2009/0317884 describes for shearing DNA to lengths of 3000 bp. (As used herein, genomic material refers to any type of material having a nucleotide sequence, such as double stranded or single stranded DNA of any length, RNA strands of any length, amplicons, plasmid DNA, etc.) For example, in one embodiment, a set of DNA fragments having an initial size greater than 5000 or 10000 bp can be sheared to lengths under 500 bp using energies of about 200 Joules and a processing time of 1-2 minutes. Such results are thought to be achieved by arranging the sample such that all portions of the sample are within about 2 mm or less of an active surface, such as a bead in the sample. For example, the sample may be provided in relatively small volumes, e.g., 1-30 microliters, along with providing one or more polymer beads in the sample, e.g., having a diameter of 0.5-3 mm, and treated with acoustic energy having a PIP of no more than about 20 W. In one specific embodiment, a sample containing relatively large genomic fragments, e.g., 2 kbp, 5 kbp, 10 kbp or more, is provided in a volume of about 15 microliters and three PTFE beads each having a diameter of about 1.5 mm are provided in the sample. The sample is processed using a PIP of about 18 W, a duty cycle of about 10-20% and for a time of 30-200 seconds. The resulting shearing causes 90%, 95%, 99% or more of the initial DNA fragments to be sheared to a length of about 200-500 bp.

In some embodiments, the sample may be provided in the vessel with a headspace above the sample being 15% or more of the vessel volume, and yet recovery of the sample after processing (such as by pipetting the sample from the vessel) may be 90% or more. That is, the sample may be acoustically treated in such a way that portions of the sample do not splash or otherwise eject from the main corpus of sample in the vessel, thus providing for improved recovery rates after processing. Such high recovery rates were unachievable with prior approaches, particularly with sample sizes below 30 microliters.

In some embodiments when shearing double stranded DNA (dsDNA), recovery of dsDNA after shearing may be 90% or greater, even after shearing dsDNA having base pair lengths of 5 kbp, 10 kbp, 48 kbp or more down to sizes under 1000 bp. This is a result that was impossible to achieve using prior approaches, particularly with shearing done at relatively low power and in short processing times. This is because dsDNA can degrade due to mechanical forces, heat and/or other factors, and the relatively high power needed with prior techniques frequently exposed the dsDNA to both high mechanical forces and heat.

In some embodiments, the vessel may have a conical shape where the sample is held that has been found particularly effective with genomic fragment shearing. For example, in one embodiment, the vessel may have a conically-shaped bottom with sidewalls arranged at an aperture angle of about 12-20 degrees. The sidewalls may be relatively thin, e.g., about 0.25 mm in thickness, and may join to a partially spherically shaped bottom of the vessel having a radius of about 1-2 mm. A depth of a 15 microliter sample in the vessel may be about 3-4 mm as measured from the inner bottom surface of the vessel to the top level of the sample.

As noted above, all portions of a sample in vessel to be acoustically treated for shearing genomic material may be located at a distance of no more than 2 mm from a surface of a nearest bead in the sample. The inventors have surprisingly found that acoustic energy applied to a sample can be significantly reduced, and processing time shortened, when shearing genomic material to base pair lengths below 1000 bp by ensuring that no more than about 2 mm separates all portions of a sample from a nearest bead or other active surface in the sample. In some embodiments, this can be achieved by providing the sample in a small volume, such as 30 microliters or less, and providing one or more beads in the sample in a size or other configuration that ensures a minimum distance between the bead(s) and all portions of the sample. The bead may be attached to a vessel wall, e.g., formed as part of the vessel, or may be contained loosely in the vessel.

In one aspect of the invention, a method for processing a sample containing genomic material includes providing a sample in a vessel, the sample including genomic material with fragments having a base pair length in excess of 2000 bp, e.g., base lengths of 10 kbp or 48 kbp or more. The vessel may have a total volume and the sample may have a sample volume of 1 microliter to about 30 microliters, e.g., 15 microliters. At least one bead may be provided in the sample to control interaction between acoustic energy and the sample, and the vessel and the at least one bead may be arranged such that all portions of the sample are no more than 2 mm away from a surface of a nearest bead. The sample and the at least one bead may be subjected to acoustic energy to cause shearing of the fragments of genomic material in the sample such that more than 90% of the fragments having a base pair length in excess of 2000 bp are sheared into fragments having a base pair length of no more than 200-1000 bp. For example, the genomic fragments may be sheared to lengths between 200-500 bp.

In some embodiments, three polymer beads may be provided in the sample, and the beads may have a diameter of about 1.5 to 2.5 mm. The vessel volume may be much larger than the sample volume, e.g., about 100 microliters, and thus there may be a substantial headspace above the sample. The headspace may have a volume that is 15%, 50% or more of the vessel volume.

In some embodiments, the vessel may be arranged to have a lower end with a conically tapered bottom having an angle of about 12-20 degrees and a wall thickness of about 0.25 mm. This arrangement has been found particularly effective in shearing DNA in small volumes.

In another aspect of the invention, a method for processing a sample containing genomic material includes providing a sample in a vessel, the sample including genomic material with fragments having a base pair length in excess of 2000 bp, e.g., 10 kbp or more. The vessel may have a total volume and the sample may have a sample volume of 1 microliter to about 30 microliters. At least one polymer bead may be provided in the sample to control interaction between acoustic energy and the sample. The sample and the at least one polymer bead may be exposed to acoustic energy to cause shearing of the fragments of genomic material in the sample such that more than 90% of the fragments having a base pair length in excess of 2000 bp are sheared into fragments having a base pair length of no more than 200-1000 bp. After shearing, the sample including sheared genomic fragments may be removed by pipette such that greater than 90%, 95% or more of the sample volume is recovered from the vessel. Such high recovery rates may be realized even if acoustic processing is done with a substantial headspace in the vessel, e.g., a headspace having a volume of 15%, 25%, 50% or more of the vessel volume. Such recovery rates were unachievable with prior acoustic shearing techniques, particularly at small volumes. In some embodiments, the beads may be arranged to bind with DNA or other genomic fragments, e.g., as described in U.S. Pat. No. 5,705,628, as well as mediate shearing of the genomic material. Such an arrangement may allow for binding and separation of selected fragments in a sample by way of the beads.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
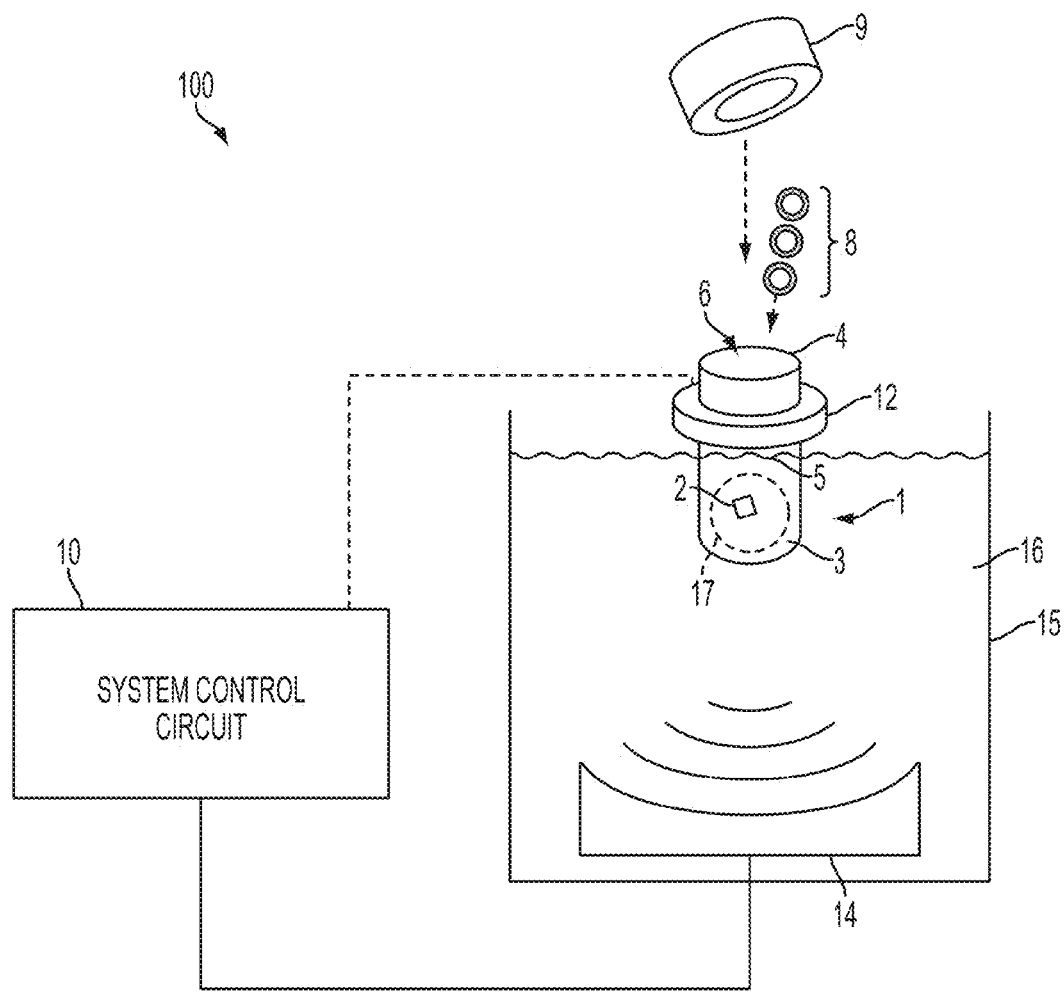
FIG. 1 shows a schematic block diagram of an acoustic treatment system that incorporates one or more aspects of the invention.

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting.

As described above, acoustic treatment systems can be useful for the homogenization and disruption of biological tissues, cells and other sample material, with the end goal of recovering target molecules from the sample material, such as DNA, RNA, proteins, and the like. In addition, such systems may be used along with aspects of the invention for DNA and/or other genomic fragment shearing, e.g., to reduce the base pair length of DNA fragments from 1,000s or 10,000s of base pairs to lengths of 200-1000 base pairs.

In accordance with aspects of the invention, a relatively small volume sample of 1 to 30 microliters may be placed in a vessel, e.g., a vessel having a volume of 2 or more times the volume of the sample, and processed with acoustic energy to shear DNA fragments in the sample that initially have a length over 2 kbp, 5 kbp, 10 kbp or more such that 90%, 95%, 99% or more of the DNA fragments end up with a length of 500 bp or less, e.g., so that most or nearly all of the fragments have a length of 200-500 bp. One or more polymer beads may be provided in the sample and arranged so that no portion of the sample is more than 2 mm away from a surface of a nearest bead. In some embodiments, each bead may have a diameter of 0.5-3 mm, e.g., preferably three beads having a diameter of about 1.5 mm may be provided in a sample. The sample may be processed with acoustic energy having a PIP of 20 watts or less and a duty cycle of 10-20% for 30-200 seconds. Recovery of the sample after shearing, such as by pipetting, may result in 90%, 95% or more of the sample being recovered.

As noted above, interaction between the sample and acoustic energy may be mediated or otherwise controlled by the one or more polymer beads immersed in the sample. The bead(s) may absorb or otherwise direct acoustic energy such that the sample is not disrupted in a way that results in splashing or other ejection of material at the interface between the sample and a gas (e.g., at the top surface of the sample in a vessel). This may help increase recovery rates after processing, e.g., 90% or more of the sample that is placed into the vessel for processing may be recovered from the vessel after acoustic processing and genomic shearing without any need to centrifuge or otherwise treat the vessel to help improve recovery rates. The beads may be a polymer sphere that is placed (e.g., loose and not connected to the vessel) in the sample so the bead is fully immersed in the sample, or a bead may be attached to or formed as part of a vessel wall.

In some embodiments, the sample may be held in a portion of the vessel that has an upwardly diverging conical shape in which the vessel sidewalls are arranged at an aperture angle of 12-20 degrees. The bottom of the vessel may have a partial spherical shape having a radius of about 1-2 mm. This arrangement of the vessel may assist in acoustic processing of the sample, e.g., by positioning the sample appropriately relative to the acoustic energy, as well as assist in improving recovery of the sample, e.g., by providing a suitably shaped and sized area from which sample can be aspirated from the vessel.

FIG. 1 shows a schematic block diagram of an acoustic treatment system 100 that incorporates one or more aspects of the invention, including one or more beads associated with a sample. It should be understood that although embodiments described herein may include most or all aspects of the invention, aspects of the invention may be used alone or in any suitable combination with other aspects of the invention. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other affects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. Although a vessel holder 12 is not necessarily required, the vessel holder 12 may serve to interface with the acoustic processing device so that the vessel 4 and the sample in the vessel is positioned in a known location relative to an acoustic field, for example, at least partially within a focal zone of acoustic energy. In this embodiment, the vessel 4 is a 130 microliter borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17. Also, the holder 12 is not limited to a device like that shown in FIG. 1, and instead may include a rack, slot, tray, gripper element, clamp, box or any other suitable arrangement for holding the vessel, or multiple vessels, in a desired location. For example, the holder 12 may include one or more multi-vessel supports and a rack. Each support may hold a plurality of vessels 4, e.g., a plurality of vessels may be held in a linear array. Each support may include an identifier, such as a barcode, RFID chip, or other component that may be read so as to identify the support and/or vessels 4 associated with the support. The rack may hold multiple supports with vessels and make it easier to physically manipulate or otherwise handle multiple vessels 4, e.g., in an automated processing environment in which one or more robotic devices manipulate vessels for acoustic or other processing. For example, the support may include a strip of material with holes into which each vessel is inserted. The rack may be arranged in the form of a multiwell plate such that vessel bottoms extending below the support may be received into a corresponding opening or well of the plate. The rack may also include an identifier so that the rack and/or supports on the rack can be identified in a automated way, e.g., by a laser scanner, optical camera, RFID tag reader or other arrangement.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others.

In this illustrative embodiment, the sample 1 includes DNA fragments 2 and a liquid 3, e.g., 15 microliters of liquid containing 20-30 nanograms of DNA fragments per microliter. (Although the DNA fragments 2 are shown schematically as a single block of material, this is for purposes of illustration only. The DNA fragments 2 may be dispersed in the liquid 3 and generally will not form a solid mass.) The DNA fragments 2 may have a base pair length of 2 kbp, 5 kbp, 10 bkp, 48 kbp or more, e.g., such that 90% or more of the DNA fragments have a base pair length over 2 kbp, 5 kbp, etc. Of course, those of skill in the art will appreciate that the sample 1 is not limited to including a liquid 3, as the sample 1 may take any suitable form, such as a solid only form, a gel, a semi-solid, etc.

In at least some embodiments, the sample volume may be less than the volume of the vessel, and thus an interface 5 will separate the sample 1 from a headspace 6 in the vessel, i.e., a gaseous region immediately above the sample 1. This arrangement may cause portions of the sample 1 to be splashed or otherwise ejected from the interface 5 in some conditions, e.g., to adhere to the vessel 4 sidewalls above the interface 5. However, the presence of one or more beads 8 in the sample 1 may reduce splashing or other sample 1 ejection from the interface 5. The beads 8 may function as a nucleation site for cavitation induced by the acoustic energy and cause shear forces created during cavitation bubble collapse to be directed to the surface of the bead, instead of to other portions in the sample. By arranging all portions of the sample within a maximum distance, e.g., 2 mm or less, of a bead surface, all portions of the sample may be positioned suitably near the bead surface (e.g., due to mixing during acoustic treatment) to experience shear or other forces that cause shearing of genomic material.

Thus, in some embodiments, the presence of the bead(s) 8 in the sample 1 having a volume of 1-30 microliters may enable shearing of DNA to occur under lower power or energy conditions than would otherwise be possible. In addition, DNA or other genomic fragments may be sheared to lengths much shorter than previously possible under relatively low power or energy conditions. DNA fragments having a base pair length of 2 kbp, 5 kbp, 10 bkp, 48 kbp or more may be sheared by acoustic energy having a PIP of 20 watts or less and a duty cycle of 10-20% in 30-200 seconds such that the 90%, 95% or more of the fragments end up with a base pair length of 200-500 bp. This is a significant and surprising improvement over prior processes.

The bead(s) may have a diameter of about 1-3 mm, with a diameter of 1.57 mm being found particularly effective in genomic shearing with sample volumes around 15 microliters. In these embodiments, three beads 8 having a 1.57 mm diameter have been found particularly useful. Beads made of PTFE have been found effective, although other polymer materials are expected to work as well. Beads having a coarse surface finish, as opposed to a polished surface finish, have been found to be effective in many applications. Generally, the beads are non-buoyant so as to remain immersed in the sample during acoustic processing, but the beads could be formed as part of a vessel wall, be attached to a vessel wall, or be neutrally buoyant. Also, although beads 8 in the illustrated embodiment are shown as spherical in shape, the beads may have a variety of shapes, e.g., like jewelry elements commonly referred to as "beads" have a variety of different shapes and sizes.

The embodiment shown in FIG. 1 also includes a cap 9 that may be used to close the open end of the vessel 4. By capping the open end of the vessel 4, an operator may be able to prevent flow out of/into the vessel 4 and/or prevent contamination of the sample 1 by the outside environment. The cap 9 may engage the vessel 4 in any way, such as by screw thread, interference fit, frictional engagement to the inner or outer surface of the vessel sidewall, etc. The use of a cap 9 is optional, and not required.

Figure 2:
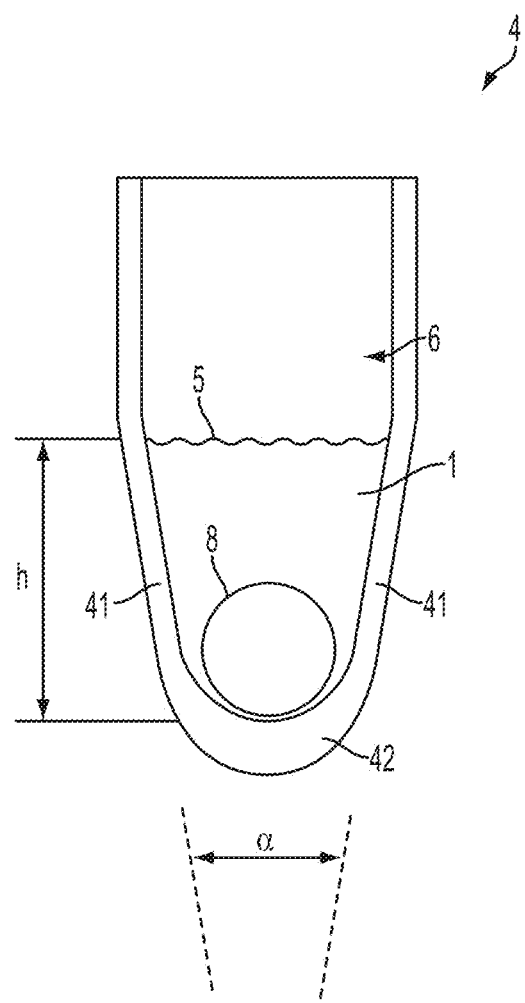
FIG. 2 is a section view of an embodiment of a sample in a vessel with a bead in accordance with aspects of the invention.

In one aspect of the invention, a vessel in which genomic material is sheared may have a conically shaped bottom arranged such that the conical walls diverge upwardly from each other at an aperture angle of about 12-20 degrees. For example, FIG. 2 shows an arrangement in which the sidewalls 41 of the vessel 4 diverge from each other at an aperture angle α of about 16 degrees. The sidewalls 41 may be relatively thin, e.g., about 0.25 mm in thickness, so as to reduce interference with acoustic energy and/or enhance heat exchange with the coupling medium 15. The extreme bottom 42 of the vessel may have a partial spherical shape with a radius of about 1-2 mm. The bottom 42 may be thicker than the sidewalls 41 as shown, or may have the same or smaller thickness. The partial spherical bottom may help with recovery of sample after processing, since sample may tend to collect at the bottom, allowing pipetting from the vessel. The sample 1 may have a height h in the vessel 4 of about 3-4 mm as measured from the inner bottom of the vessel to the interface 5.

Figure 3:
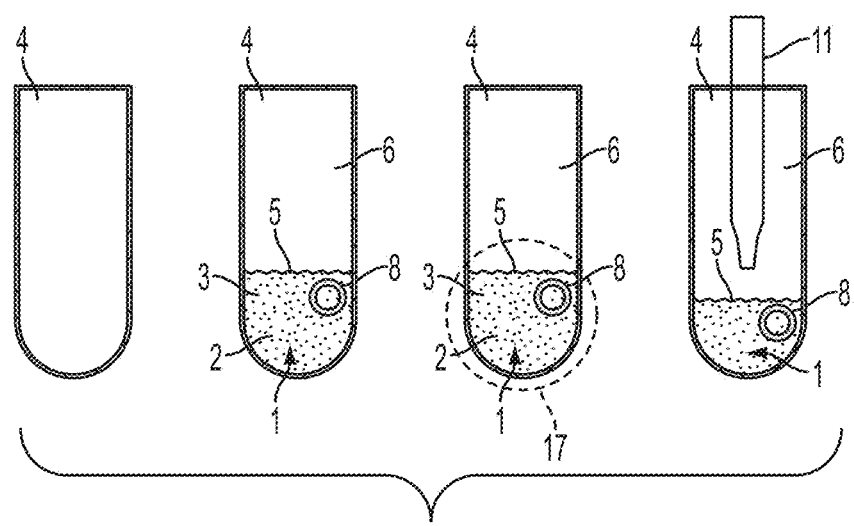
FIG. 3 shows steps in an illustrative method for providing a sample in a vessel with a bead in accordance with aspects of the invention.

FIG. 3 outlines steps in a method of shearing genomic material in accordance with aspects of the invention. A vessel 4 is provided having a vessel volume, which may be 50-150 microliters or more (or less). The vessel 4 may be made of glass or a polymer. Glass materials may aid in heat transfer to a coupling medium, and some polymer materials have been found to aid in genomic material shearing. The vessel 4 may have a conically-shaped bottom with sidewalls upwardly diverging at an angle of about 12-20 degrees, e.g., as shown in FIG. 2. The extreme bottom of the vessel 4 may have a partial spherical shape. This arrangement has been found particularly useful in shearing DNA in a sample volume of about 15 microliters. Alternately, the vessel 4 may be a cylindrical tube with vertical sidewalls and a flat or spherical bottom, as shown.

Next, a sample 1 containing genomic fragments 2 and liquid 3 may be placed in the vessel 4. The sample 1 may have a volume of about 1 to 30 microliters, with a volume of 15 microliters having been found in some examples to be particularly suitable for effective DNA shearing. The sample 1 may have a height in the vessel 4 of about 3-4 mm above the vessel inner bottom. Genomic fragments in the sample may be provided at a concentration of about 20-30 nanograms/microliter, and may have fragment lengths of more than 2 kbp, 5 kbp, 10 kbp, 48 kbp or more. One to three polymer beads, e.g., made of PTFE having a diameter of 1-3 mm may be provided in the sample 1 so the beads are immersed in the sample. Providing three spherical PTFE beads having a diameter of about 1.57 mm in a 15 microliter sample has been found particularly suitable for shearing DNA.

Thereafter, the sample 1 may be treated with acoustic energy to shear the DNA or other genomic material, such as RNA, in the sample 1. The acoustic energy may have a frequency range of between about 100 kilohertz and about 100 megahertz and have a focal zone 17 with a width of about 2 centimeters or less. The focal zone 17 may be positioned so that the entire sample 1 is located in the focal zone 17, or so that a portion of the sample is in the focal zone 17. In some embodiments, the sample may move through the focal zone 17, whether by moving the focal zone 17 relative to the vessel 4 or moving the vessel 4 relative to the focal zone 17. The acoustic energy may have a peak incident power (PIP) of 20 watts or less and a duty cycle of 10-20%. The sample 1 may be treated with the acoustic energy over a time period of 30-200 seconds. As a result, 90%, 95%, 99% or more of the genomic material having a relatively long fragment length may be sheared to fragments having a length of 200-1000 base pairs. In some embodiments, 99% or more of the initial genomic material may be sheared to have a base pair length of 200-500 bp.

With acoustic processing complete, the sample may be removed from the vessel 4. In some embodiments, the sample 1 may be aspirated by a pipette 11 that pushes the beads 8 to the side, as necessary, as the pipette tip opening is lowered below the surface of the sample fluid 3. Recovery of the sample 1 may be greater than 90%, or 95%. That is, of a volume or mass of sample initially provided in the vessel 4 for treatment, 90% or 95% or more of the sample may be removed from the vessel, e.g., by pipetting. In other embodiments, once shearing is complete, other processes may be performed on the sample while in the vessel, such as PCR amplification, stirring, catalyzing, heating, disruption of molecular bonds, or any other appropriate process. Such processes may be performed using acoustic energy, or not, e.g., PCR processing may be performed by a standard thermocycler machine.

A few illustrative examples of shearing DNA using methods and systems according to the invention are described below.

Example One

Figure 4:
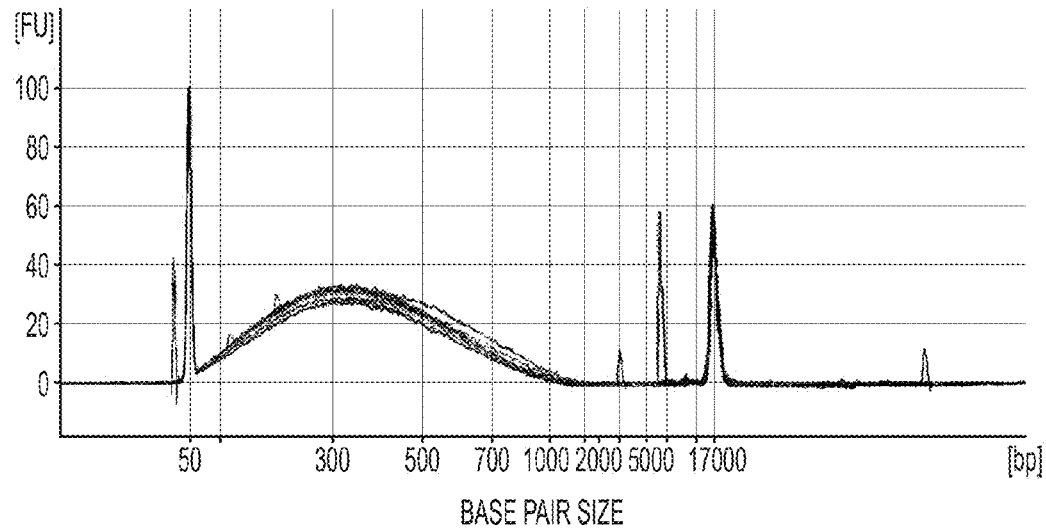
FIG. 4 shows a DNA fragment size distribution according to Example One below.
Figure 8:
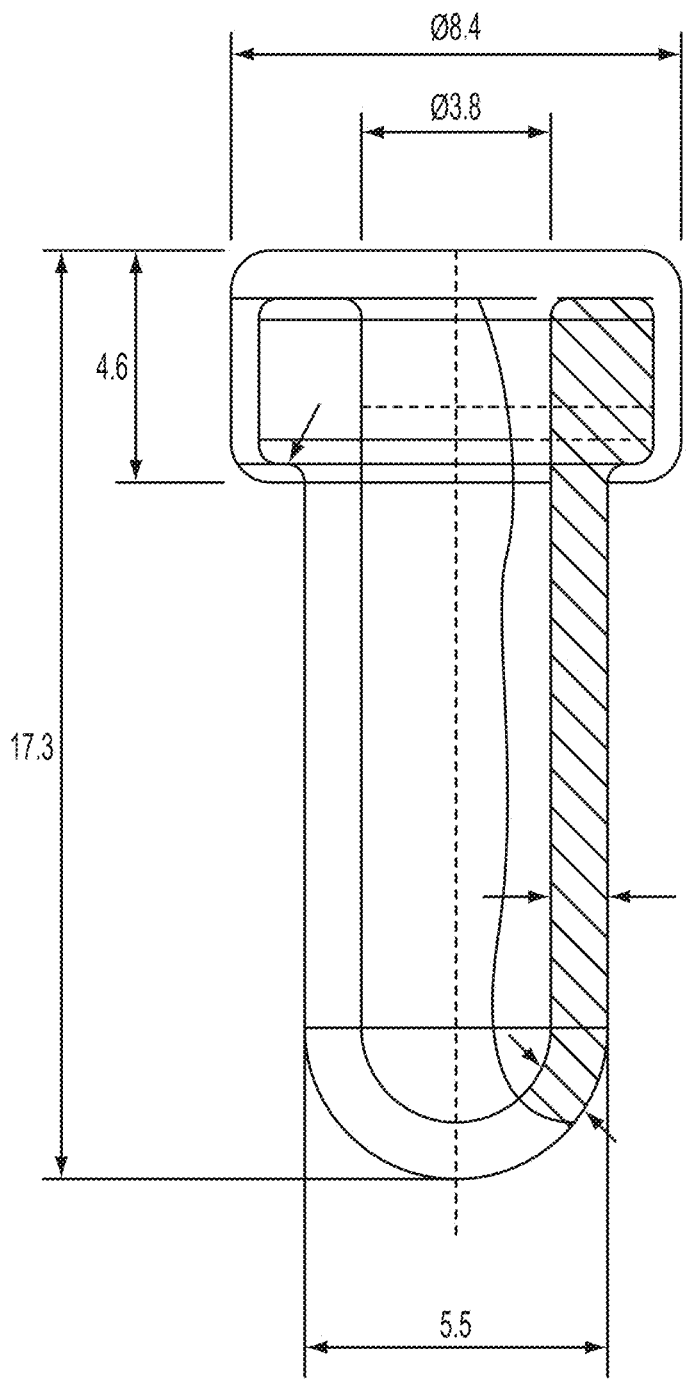
FIG. 8 shows a vessel used to hold a sample in Example One below.

A vessel having a volume of 130 microliters was provided with a 15 microliter sample containing lambda DNA (i.e., DNA fragments having a base pair length of 48 kbp or more) at a concentration of about 28 nanograms/microliter. Three 1.57 mm PTFE beads were provided in the sample as well, and the borosilicate glass vessel having a spherical bottom was closed by a split septum, as shown in FIG. 8. (Dimensions in FIG. 8 are in millimeters.) The sample was acoustically treated using a Covaris S220 ultrasonicator set to provide a PIP of 18 watts, a 20% duty cycle and 50 cycles per burst for 60 seconds. Some splashing of the sample was observed during acoustic treatment. The results of processing are shown in FIG. 4. More than 95% of the lambda DNA fragments were sheared to DNA fragments having a length under 1000 bp, with an average base pair length of the sheared DNA being about 336 bp. More than 75% of the sheared DNA had a base pair length of 100-500 bp. Also of note is that more than 96% of the sample was recovered from the vessel after acoustic treatment, and more than 93% of the DNA material initially provided in the vessel was recovered by pipetting. The experiment was repeated 12 times, and a coefficient of variation of less than 4% was determined, i.e., the results of DNA shearing were found to be highly repeatable and consistent. The total energy of about 216 Joules to shear the lambda DNA is far less than expected, and is thought to be due at least in part to the relatively small sample size and the presence of three beads in the sample.

Example Two

Figure 5:
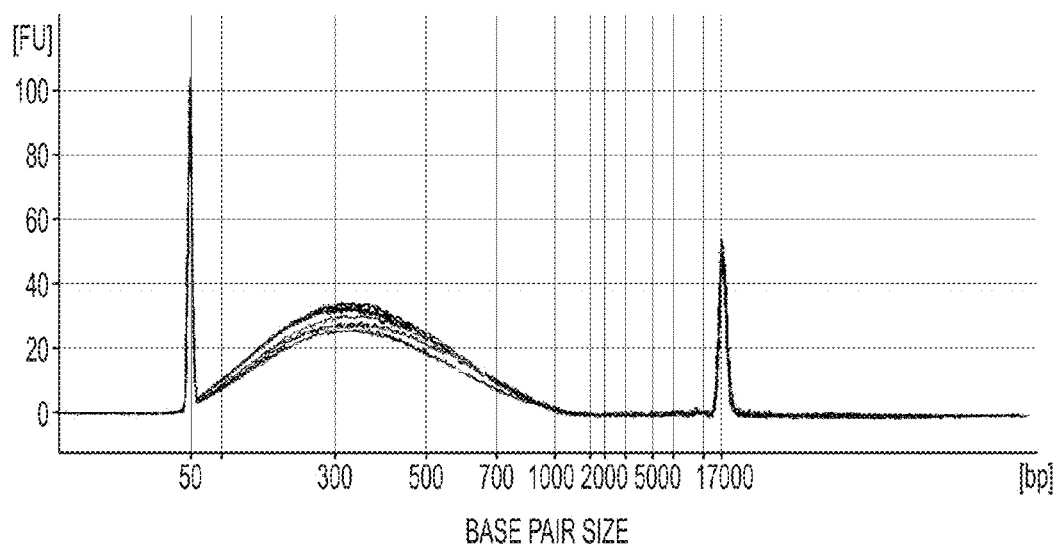
FIGS. 5 and 6 show DNA fragment size distribution according to Example Two below.
Figure 6:
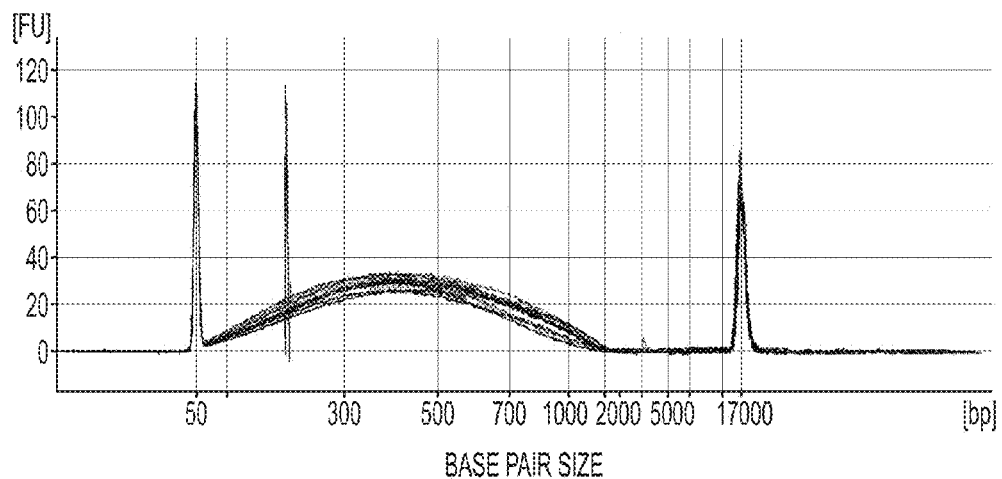

Example One was repeated, except that the samples were processed with two 1.57 mm beads and with one 1.57 mm beads. (Processing time for the single bead experiment was increased from 60 seconds to 120 seconds.) The results are shown, respectively, in FIGS. 5 and 6. In both experiments, more than 90% of the lambda DNA fragments were sheared to DNA fragments having a length under 1000 bp, with an average base pair length of the sheared DNA being about 332 bp for two beads, and about 412 bp for one bead. The coefficient of variation for two beads was about 4.0%, and for one bead was about 7.2% based on 12 repeat experiments for each.

Example Three

Figure 7:
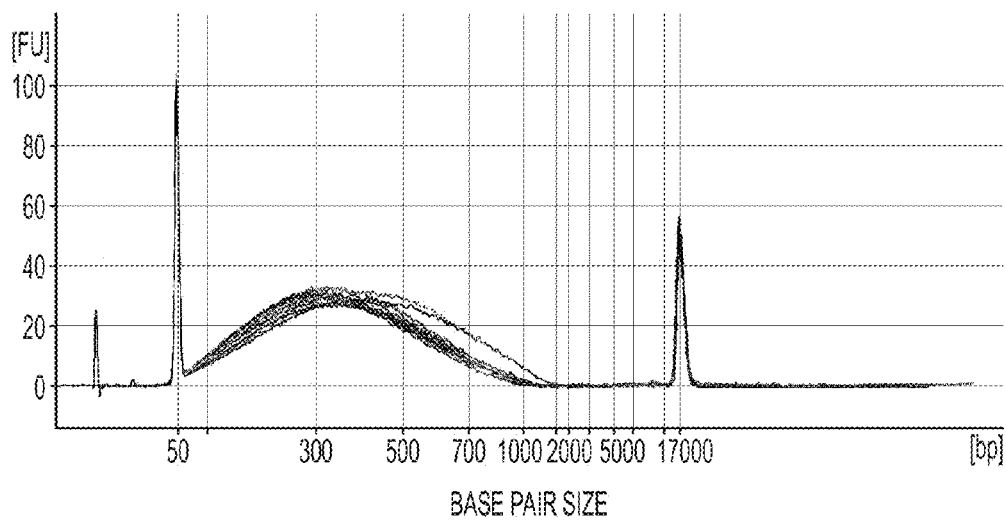
FIG. 7 shows a DNA fragment size distribution according to Example Three below.

Example One was repeated, except that the samples were processed using one 2.36 mm bead, i.e., a larger bead than those used in Examples One and Two. The results are shown in FIG. 7. More than 95% of the lambda DNA fragments were sheared to DNA fragments having a length under 1000 bp, with an average base pair length of the sheared DNA being about 337 bp. The coefficient of variation was about 10.5% based on 12 repeat experiments, i.e., a significant drop in repeatability versus the smaller bead sizes. Recovery of the sample volume was about 80%, also significantly less than that found in the three bead example above.

Example Four

Example One was repeated twice, except that lambda DNA concentrations were dropped to 15 nanograms/microliter and 7.5 nanograms/microliter, respectively. Shearing results were found to be nearly identical to that of Example One, i.e., average base pair lengths of about 323 bp and 317 bp were found for each different DNA concentration, along with coefficient of variation values of 4.4% and 1.8%, respectively. This shows that the technique of Example One can be applied to different genomic material concentrations, at least those below about 30 nanograms/microliter.

Example Five

A set of experiments were run to compare the shearing performance of two different types of vessels, i.e., a sample tube having vertical sidewalls and a spherical bottom, and a sample tube arranged like that in FIG. 2. 450 nanograms of lambda DNA in a 15 microliter sample containing a single 1.57 mm PTFE bead were sheared to about a 200 bp average using acoustic energy having a PIP of 18 watts, a 20% duty cycle and 50 cycles per burst. Samples in the vertical sidewall vessel were processed for 250 seconds, and samples in the conically-shaped bottom vessel were processed for 120 seconds. (Additional processing time was required for the vertical sidewall tube to achieve the about 200 bp average result.) The actual average for the sheared DNA in the vertical sidewall tube was about 255 bp, with a coefficient of variation of about 6.3%. The average for the sheared DNA in the conically-shaped bottom vessel was about 226 bp with a coefficient of variation of about 1.0%. Thus, it was surprisingly found that the vessel shape had a significant impact on shearing results, with the conically-shaped bottom vessel requiring about half (or less) energy to achieve a lower average base pair size and with significantly better repeatability.

Example Six

Example Five was repeated, except that the DNA was sheared to an average base pair size of about 300 bp.

Conditions were identical, except that the vertical sidewall vessel samples were processed for 120 seconds, and samples in the conically-shaped bottom vessel were processed for 60 seconds. (Note that significantly less energy is required to shear to an average base pair size of 300 bp versus 200 bp.) The average for the sheared DNA in the vertical sidewall tube was about 361 bp, with a coefficient of variation of about 5.0%. The average for the sheared DNA in the conically-shaped bottom vessel was about 312 bp with a coefficient of variation of about 2.0%. Here again, it was surprisingly found that the vessel shape had a significant impact on shearing results, with the conically-shaped bottom vessel requiring about half (or less) energy to achieve a lower average base pair size and with significantly better repeatability.

As described above, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A method for processing a sample containing genomic material, comprising:
    providing a sample in a vessel, the sample including genomic material with fragments having a base pair length in excess of 2000 bp, the vessel having a total volume and the sample having a sample volume of 1 microliter to about 30 microliters;
    providing at least one bead in the sample to control interaction between acoustic energy and the sample, the vessel and at least one bead being arranged such that all portions of the sample are no more than 2 mm away from a surface of a nearest bead; and
    subjecting the sample and the at least one bead to acoustic energy to cause shearing of the fragments of genomic material in the sample such that more than 90% of the fragments having a base pair length in excess of 2000 bp are sheared into fragments having a base pair length of no more than 200-1000 bp.

2. The method of claim 1, wherein the step of providing includes providing three polymer beads in the sample.

3. The method of claim 1, wherein the at least one bead has a diameter of about 1.5 to 2.5 mm.

4. The method of claim 1, wherein the sample volume is about 15 microliters.

5. The method of claim 4, wherein the step of providing includes providing three polymer beads having a diameter of about 1.5 mm in the sample.

6. The method of claim 1, wherein the vessel volume is about 100 microliters.

7. The method of claim 1, wherein the fragments having a base pair length in excess of 2000 bp are sheared into fragments having a base pair length under 500 bp.

8. The method of claim 1, wherein the vessel has a headspace of at least 15% of the vessel volume.

9. The method of claim 1, further comprising pipetting at least 90% of the sample volume from the vessel after the subjecting step.

10. The method of claim 1, wherein the vessel has a lower end with a conically tapered bottom having an angle of about 12-20 degrees and the vessel has a wall thickness of about 0.25 mm.

11. The method of claim 1, wherein more than 75% of the fragments having a base pair length in excess of 2000 bp are sheared into fragments having a base pair length of no more than 100-500 bp.

12. The method of claim 1, wherein the fragments provided in the vessel have a base pair length in excess of 10 kbp and are sheared into fragments having an average base pair length of no more than 200-500 bp.

13. A method for processing a sample containing genomic material, comprising:
    providing a sample in a vessel, the sample including genomic material with fragments having a base pair length in excess of 2000 bp, the vessel having a total volume and the sample having a sample volume of 1 microliter to about 30 microliters;

providing at least one polymer bead in the sample to control interaction between acoustic energy and the sample;

subjecting the sample and the at least one polymer bead to acoustic energy to cause shearing of the fragments of genomic material in the sample such that more than 90% of the fragments having a base pair length in excess of 2000 bp are sheared into fragments having a base pair length of no more than 200-1000 bp; and removing the sample including sheared genomic fragments by pipette such that greater than 90% of the sample volume is recovered from the vessel.

14. The method of claim 13, wherein greater than 95% of the sample volume is recovered from the vessel.

15. The method of claim 13, wherein an initial mass of genomic material is provided in the vessel with the sample, and the step of removing includes recovering at least 90% of the initial mass of genomic material.

16. The method of claim 15, wherein at least 95% of the initial mass of genomic material is recovered from the vessel.

17. The method of claim 13, wherein the genomic material has fragments with a base pair length in excess of 10000 bp.

18. The method of claim 13, wherein the subjecting step is performed with a headspace in the vessel of 15% or more of the vessel total volume.

19. The method of claim 13, wherein the subjecting step is performed over a time period of 30-200 seconds.

20. The method of claim 13, wherein the step of providing includes providing three polymer beads in the sample.

21. The method of claim 13, wherein the at least one bead has a diameter of about 1.5 to 2.5 mm.

22. The method of claim 13, wherein the sample volume is about 15 microliters.

23. The method of claim 22, wherein the step of providing includes providing three polymer beads having a diameter of about 1.5 mm in the sample.

24. The method of claim 13, wherein 75% or more of the fragments having a base pair length in excess of 2000 bp are sheared into fragments having a base pair length under 500 bp.

25. The method of claim 13, wherein the at least one bead is made of PTFE.

26. The method of claim 13, wherein the vessel has a lower end with a conically tapered bottom having an angle of about 12-20 degrees and the vessel has a wall thickness of about 0.25 mm.

27. The method of claim 13, wherein more than 95% of the fragments having a base pair length in excess of 2000 bp are sheared into fragments having an average base pair length of no more than 200-500 bp.

28. A method for processing a sample containing genomic material, comprising:

providing a sample in a vessel, the sample including genomic material with fragments having a base pair length in excess of 3000 bp, the vessel having a total volume and the sample having a sample volume of 1 microliter to about 30 microliters;

providing at least one polymer bead in the sample to control interaction between acoustic energy and the sample; and subjecting the sample and the at least one polymer bead to acoustic energy for 30-200 seconds at a peak incident power of 20 W or less to cause shearing of the fragments of genomic material in the sample such that more than 95% of the fragments having a base pair length in excess of 2000 bp are sheared into fragments having a base pair length of no more than 200-1000 bp.

29. The method of claim 28, wherein the step of providing includes providing three polymer beads in the sample.

30. The method of claim 28, wherein the at least one bead has a diameter of about 1.5 to 2.5 mm.

31. The method of claim 28, wherein the sample volume is about 15 microliters.

32. The method of claim 31, wherein the step of providing includes providing three polymer beads having a diameter of about 1.5 mm in the sample.

33. The method of claim 28, wherein the vessel volume is about 100 microliters.

34. The method of claim 28, wherein 75% or more of the fragments having a base pair length in excess of 2000 bp are sheared into fragments having a base pair length under 500 bp.

35. The method of claim 28, wherein the vessel has a headspace of at least 15% of the vessel volume.

36. The method of claim 28, further comprising pipetting at least 90% of the sample volume from the vessel after the subjecting step.

37. The method of claim 28, wherein the at least one bead is made of PTFE and has a coarse surface finish.

38. The method of claim 28, wherein the vessel has a lower end with a conically tapered bottom having an angle of about 12-20 degrees and the vessel has a wall thickness of about 0.25 mm.

39. The method of claim 28, wherein more than 95% of the fragments having a base pair length in excess of 2000 bp are sheared into fragments having an average base pair length of no more than 200-500 bp.

* * * * *

UNITED STATES PATENT AND TRADEMARK OFFICE
CERTIFICATE OF CORRECTION

| | | |
|---|---|---|
| PATENT NO. | : 9,486,756 B2 | Page 1 of 1 |
| APPLICATION NO. | : 14/534506 | |
| DATED | : November 8, 2016 | |
| INVENTOR(S) | : James A. Laugharn, Jr. | |

It is certified that error appears in the above-identified patent and that said Letters Patent is hereby corrected as shown below:

In the Specification

Column 7, Line 16, "10 bkp" should read -- 10kbp --

Column 7, Line 48, "10 bkp" should read -- 10kbp --

Signed and Sealed this
Fourteenth Day of February, 2017

Michelle K. Lee
*Director of the United States Patent and Trademark Office*